United States Patent
Martinez et al.

(10) Patent No.: US 12,364,656 B2
(45) Date of Patent: **\*Jul. 22, 2025**

(54) DEPILATORY COMPOSITIONS COMPRISING AMINOALKYLPROPANOL

(71) Applicant: Reckitt Benckiser Health Limited, Slough (GB)

(72) Inventors: Lorea Oria Martinez, Leeds (GB); Bronte Arabella Weir, Dubai (AE); Scott Seville, Hull (GB); Diane Marie Pavis, Hull (GB); Victoria Walker, Hull (GB)

(73) Assignee: Reckitt Benckiser Health Limited, Slough (GB)

( * ) Notice: Subject to any disclaimer, the term of this patent is extended or adjusted under 35 U.S.C. 154(b) by 363 days.

This patent is subject to a terminal disclaimer.

(21) Appl. No.: 17/685,732

(22) Filed: Mar. 3, 2022

(65) Prior Publication Data

US 2022/0265536 A1 Aug. 25, 2022

Related U.S. Application Data

(63) Continuation of application No. 16/069,692, filed as application No. PCT/GB2017/050077 on Jan. 12, 2017, now Pat. No. 11,266,586.

(30) Foreign Application Priority Data

Jan. 12, 2016 (GB) .................................... 1600586

(51) Int. Cl.
| | |
|---|---|
| A61K 8/41 | (2006.01) |
| A61K 8/02 | (2006.01) |
| A61K 8/04 | (2006.01) |
| A61K 8/19 | (2006.01) |
| A61K 8/42 | (2006.01) |
| A61K 8/46 | (2006.01) |
| A61K 8/73 | (2006.01) |
| A61K 8/81 | (2006.01) |
| A61Q 9/04 | (2006.01) |

(52) U.S. Cl.
CPC .............. *A61K 8/41* (2013.01); *A61K 8/0208* (2013.01); *A61K 8/042* (2013.01); *A61K 8/046* (2013.01); *A61K 8/19* (2013.01); *A61K 8/42* (2013.01); *A61K 8/46* (2013.01); *A61K 8/73* (2013.01); *A61K 8/8152* (2013.01); *A61Q 9/04* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 4,618,344 | A | 10/1986 | Wells |
| 2004/0219118 | A1 | 11/2004 | Slavtcheff et al. |
| 2015/0283042 | A1 | 10/2015 | Benn et al. |

FOREIGN PATENT DOCUMENTS

| | | |
|---|---|---|
| EP | 1799177 B1 | 6/2007 |
| EP | 2561856 A1 | 2/2013 |
| GB | 1064388 A | 4/1967 |
| GB | 1291377 A | 4/1972 |
| GB | 1329029 A | 9/1973 |
| JP | H0812531 A | 1/1996 |
| WO | 2008034178 A1 | 3/2008 |
| WO | 2012148948 A1 | 11/2012 |

OTHER PUBLICATIONS

AnGus Chemical Company Product Sales Sheet, published May 2015, Neutralizing Amines: Neutralizing Amines for Personal Care Ingredients.
Indian Examination Report dated Jul. 2, 2020 issued in corresponding India Patent Application No. 201847029438.
"Fresh-Scented Body Hair Removal Spray Foam," MINTEL, http://www.gnpd.com; Aug. 31, 2015.
Anonymous, "Hydroxyethyl Urea in Personal Care and Hair Spray Formulations with acrylates copolymer to Improve Aesthetic and Spray Properties," ip.com Journal, Aug. 15, 2006.
Combined Search and Examination Report issued in priority application No. GB1600586.0 mailed Oct. 6, 2016.
International Search Report and Written Opinion issued in International Application No. PCT/GB2017/050077 mailed Jun. 20, 2017.

*Primary Examiner* — Tigabu Kassa
(74) *Attorney, Agent, or Firm* — Dunlap Codding, P.C.

(57) ABSTRACT

The present invention is directed to depilatory compositions comprising a depilatory active, alkali metal hydroxide and an aminoalkylpropanol. The compositions have a pH in the range of from 10 to 12.5. The depilatory active preferably contains a thiol group, the alkali metal hydroxide preferably comprises potassium hydroxide and the aminoalkylpropanol preferably comprises aminomethylpropanol. The composition is preferably a gel, mousse, foam, cream, lotion or peelable film, especially a translucent or transparent gel. The depilatory compositions provide effective hair removal yet are well tolerated by the skin and allow for acceptable application times of the composition. The present invention further provides a depilatory composition comprising urea, a carbomer, and a gum; these compositions may or may not comprise aminoalkylpropanol.

24 Claims, No Drawings

DEPILATORY COMPOSITIONS COMPRISING AMINOALKYLPROPANOL

CROSS-REFERENCE TO RELATED APPLICATIONS

This application is a Continuation of U.S. patent application Ser. No. 16/069,692 filed 12 Jul. 2018, which is a U.S. National Phase of International Patent Application No. PCT/GB2017/050077, filed on 12 Jan. 2017, which claims priority to United Kingdom application Serial No. 1600586.0 filed 12 Jan. 2016. The entire contents of these applications are incorporated herein by reference in their entirety.

TECHNICAL FIELD

The present invention relates to a depilatory composition comprising a depilatory active, an alkali metal hydroxide and an aminoalkylpropanol and having a pH at 20° C. in the range 10 to 12.5. The compositions provide effective hair removal within an acceptable contact time yet are well tolerated by the skin. A method of removing hair and a method of producing the compositions are also provided.

BACKGROUND

Compositions for removing superfluous hair from mammals are well known. Such compositions include depilatory compositions which comprise a compound that degrades the keratin within the hair thus weakening it and allowing for removal. The depilatory compositions are applied to the area containing the superfluous hair, allowed to remain thereon to degrade the hairs and then removed from the area together with the degraded hairs.

Depilatory compositions of this type typically comprise depilatory compounds which have a thiol group, such as potassium thioglycolate, and also typically contain potassium hydroxide to provide a high pH which aids hair removal efficacy. However, there is a significant disadvantage in using such compositions in that they can irritate and even damage the skin as a result of the high pH (usually above 12). The potential for skin irritation and damage increases with the length of time that the depilatory compositions are left in contact with the skin. Unfortunately in order to obtain acceptable hair removal it can be necessary to leave the depilatory composition in contact with the skin/hair for a longer contact time than the skin can easily tolerate without being susceptible to irritation or even damage.

There is therefore a need within the art to provide depilatory compositions which ameliorate one or more of the above disadvantages with known compositions. In particular there is a need within the art to provide depilatory compositions which provide for effective hair removal yet without unduly irritating or damaging the skin. In particular there is a need to provide such compositions which can be used for effective hair removal within an acceptable application time, preferably less than 10 minutes and ideally 7 minutes or less in order to reduce the likelihood of skin irritation/damage.

Furthermore, there is a need in the art to be able to produce such compositions easily and conveniently without unacceptable levels of thickening (which can lead to production and processing difficulties). There is a further need in the art to produce such compositions which are stable on storage and which show good pH stability.

It is an object of the present invention to provide depilatory compositions comprising a depilatory active which address one or more of the above disadvantages. In particular, it is an object of the present invention to provide such depilatory compositions which provide effective hair removal yet which are well tolerated by the skin. It is a further object of the present invention to provide such compositions which exhibit good hair removal properties with a contact time of 10 minutes or less, preferably 7 minutes or less. It is a further object of the present invention to provide such compositions which can be produced easily, and, which are stable on storage and which show good pH stability.

Surprisingly, it has been found that one or more of the aforementioned disadvantages can be addressed by the inclusion of an aminoalkylpropanol, especially aminomethylpropanol, in depilatory compositions comprising a depilatory active and by formulating such a composition to have a pH at 20° C. in the range of from 10 to 12.5.

GB1 064 388 discloses substituted thiol based depilatory actives used in an emollient base which provides a mantle to prevent skin irritation by the depilatory actives.

GB 1 329 029 discloses a self-heating depilatory compositions comprising a thioglycollate. A pH of 10 to 12.5 is disclosed for the compositions.

JP 08-012531 discloses hair growing agents which may comprise potassium hydroxide and 2 amino-2-methylpropanol. No examples are given of depilatory compositions comprising 2 amino-2-methylpropanol. The compositions are also described as depilatory compositions in the document but no depilatory actives are disclosed.

SUMMARY OF INVENTION

According to an aspect of the present invention, there is provided a depilatory composition comprising: a depilatory active; an alkali metal hydroxide selected from the group consisting of sodium hydroxide and/or potassium hydroxide; and an aminoalkylpropanol, wherein at 20° C. the composition has a pH in the range of from 10 to 12.5.

In another aspect, the present invention provides a method of removing hair from the bodily surface of a mammal, the method comprising: (i) applying a composition according any of the embodiments described herein to the bodily surface of a mammal from where it is desired to remove hair; (ii) allowing the composition to contact the bodily surface for a period of time of from 1 to 10 minutes; and (iii) subsequently removing at least a portion of the composition from the bodily surface.

In another aspect, the present invention provides a method of producing a composition according any of the embodiments described herein, the method comprising: (i) providing an intermediate composition comprising the depilatory active and the alkali metal hydroxide; and (ii) adding the aminoalkylpropanol to the intermediate composition.

In another aspect, the present invention provides a depilatory composition comprising: a depilatory active; urea; a carbomer; and a gum.

DETAILED DESCRIPTION OF THE INVENTION

According to a first aspect of the present invention, there is provided a depilatory composition comprising: a depilatory active; an alkali metal hydroxide selected from the group consisting of sodium hydroxide and/or potassium hydroxide; and an aminoalkylpropanol, wherein at 20° C. the composition has a pH in the range of from 10 to 12.5.

It has been found that compositions according to the present invention provide for good hair removal properties yet are well tolerated by the skin. Furthermore, the compositions provide for good hair removal within acceptable contact times with the skin/hair which further reduces the risk of skin irritation/damage. Typically, a contact time of 10 minutes or less is required for the compositions of the present invention to provide for effective hair removal and contact times of 7 minutes or less can be provided according to some embodiments of the invention.

According to a second aspect of the present invention there is provided a method of removing hair from a bodily surface of a mammal, the method comprising the steps of:
i) applying a composition according to any one of the preceding claims to the bodily surface of a mammal from where it is desired to remove hair,
ii) allowing the composition to contact the bodily surface for a period of time of from 1 to 10 minutes, and
iii) removing the composition from the bodily surface.

The method of the second aspect of the present invention provides for the same advantages as the first aspect of the invention with respect to the advantages regarding hair removal efficiency and skin tolerance.

According to a third aspect of the present invention there is provided a method of producing a composition according to the present invention, wherein the method comprises the step of the addition of the aminoalkylpropanol to a composition comprising a depilatory active and an alkali metal hydroxide.

It has been found that this method of the present invention provides a convenient way of producing the compositions of the invention without undue thickening of the compositions occurring.

The compositions of the present invention comprise a depilatory active, an alkali metal hydroxide selected from sodium hydroxide and/or potassium hydroxide and an aminoalkylpropanol, and the compositions have a pH at 20° C. the range of from 10 to 12.5.

i) Definitions

By the term "depilatory active" as used herein is meant a compound which acts upon the keratin in the hair to chemically degrade it by breaking down the disulphide bonds in the keratin. This chemical degradation weakens the hair and allows for the degraded, and thus weakened, hair to be removed. It does not include rosin materials or waxes or any other ingredient(s) which do/does not exert a chemical-degradation action on the hair, but which rather, provide(s) an epilatory effect by adhering to the hair.

By the term "bodily surface" as used herein is meant an external surface of a mammal including but not limited to the head, face and body. Mucosal membranes are not included within this definition of "bodily surface".

The pH of the compositions as referred to herein is the pH of the composition at 20° C. Unless otherwise stated all amounts are given herein as wt % based on the total weight of the composition.

ii) Form of the Compositions

The depilatory compositions of the present invention may be of any suitable form. Preferred forms for the compositions include gels, mousses, foams, creams, lotions or peelable films. The form may be chosen according to the intended area of application for the compositions. Especially preferred forms of the compositions include gels, creams, mousses, foams and peelable films. Some consumers prefer to use a composition which is not opaque. Thus according to one embodiment of the invention the compositions are translucent or transparent. Transparent or translucent gels, mousses, foams or peelable films are preferred according to one embodiment of the present invention. Transparent or translucent gels are especially preferred.

iii) Depilatory Active

The depilatory active present in the compositions of the invention may be any compound which provides for the removal of hair by a chemical reaction, such as by degrading the keratin present in the hair. It is preferred that the depilatory active contains a thiol group and most especially that the depilatory active which contains a thiol group is selected from one or more of the group consisting of potassium thioglycolate, calcium thioglycolate, thioglycolic acid, dithioerythritol, thioglycerol, thioglycol, thioxanthine, thiosalicylic acid, N-acetyl-L-cysteine, lipoic acid, sodium dihydrolipoate 6,8-dithiooctanoate, sodium 6,8-diothiooctanoate, a hydrogen sulphide salt, 2-mercaptopropionic acid, 3-mercaptopropionic acid, thiomalic acid, ammonium thioglycolate, glyceryl monothioglycolate, monoethanolamine thioglycolate, monoethanolamine diammoniumdithiodiglycolate, ammonium thiolactate, monoethanolamine thiolactate, thioglycolamide, homocysteine, cysteine, glutathione, dithiothreitol, dihydrolipoic acid, 1,3-dithiopropanol, thioglycolamide, thioglycol-hydrazine, keratinase, guanidine thioglycolate, and cysteamine.

According to one embodiment of the invention the depilatory active comprises at least one of potassium thioglycolate, calcium thioglycolate and thioglycolic acid, in particular at least one of potassium thioglycolate and thioglycolic acid. Typically the compositions include a thioglycolic acid salt, such as potassium thioglycolate and/or calcium thioglycolate. Whilst the compositions are typically prepared using the thioglycolates, during storage at least some of the thioglycolate is converted to thioglycolic acid.

The depilatory active is preferably present in an amount of from 0.5 to 10 wt % more preferably 1 to 9 wt %, such as 1.5 to 7 wt %, e.g. 2 to 6 wt % based on the total weight of the depilatory composition. It is preferred that the compositions of the invention comprise potassium thioglycolate and/or sodium thioglycolate and/or thioglycolic acid in the aforementioned amounts (in total if more than one of these are present). It is especially preferred that the compositions comprise the aforementioned amounts of potassium thioglycolate and/or thioglycolic acid.

iv) Alkali Metal Hydroxide

The compositions of the present invention further comprise an alkali metal hydroxide selected from sodium hydroxide and/or potassium hydroxide as a source of alkalinity. It is preferred that at least 50 wt % thereof is potassium hydroxide (based on the total weight of the alkali metal hydroxide in the composition).

The alkali metal hydroxide is preferably present in a total amount of from 0.5 to 5 wt % (by weight of the composition), more preferably 1 to 3 wt %, such as 1.5 to 2.5 wt %, e.g. 1.75 to 2.25 wt %. It is especially preferred that the compositions of the invention comprise potassium hydroxide in these amounts, most especially 1.5 to 2.5 wt %.

The amount of the alkali metal hydroxide added will depend upon the desired pH of the depilatory composition and other formulation considerations. However it has been found that good hair removal properties and acceptable contact times combined with the compositions being well tolerated by the skin are achieved with compositions according to the invention which contain the above amounts of the alkali metal hydroxide.

v) Aminoalkylpropanol

The compositions of the invention comprise an aminoalkylpropanol.

Without wishing to be bound by theory, the presence of the aminoalkylpropanol, is believed to allow for the depilatory compositions of the invention to be formulated at a pH at 20° C. in the range of from 10-12.5, (which is lower than many depilatory compositions which act by chemically degrading the keratin in the hair) yet still provide for effective hair removal and have a contact time in use which is sufficiently short that it does not lead to unacceptable levels of skin irritation.

Any aminoalkylpropanol may be used according to the present invention, such as aminomethylpropanol, aminoethylpropanol or aminopropylpropanol. However it is preferred that the aminoalkylpropanol comprises aminomethylpropanol and preferably is aminomethylpropanol.

The aminoalkylpropanol is preferably present in the compositions an amount of from 0.2 to 10 wt %, based on the total weight of the composition. It is especially preferred that the aminoalkylpropanol is present in an amount of from 0.5 to 5 wt %, more preferably 0.75 to 4.5 wt %, such as 1 to 4 wt %, and most especially 1.5 to 3.5 wt %. It is especially preferred that the compositions of the invention comprise the aforementioned amounts of aminomethylpropanol.

According to one embodiment of the invention the weight ratio of the aminoalkylpropanol to alkali metal hydroxide is in the range 3:1 to 1:1, preferably 2:1 to 1:1, such as 1.5:1 to 1:1. It is especially preferred that in the compositions there is weight ratio of the aminomethylpropanol to potassium hydroxide of from 3:1 to 1:1, preferably 2:1 to 1:1, such as 1.5:1 to 1:1.

It is especially preferred that the compositions of the invention comprise potassium thioglycolate and/or thioglycolic acid, potassium hydroxide and aminomethylpropanol. It is further preferred that the composition comprises from 2 to 6 wt % potassium thioglycolate and/or thioglycolic acid, from 0.5 to 5 wt % potassium hydroxide and from 0.75 to 4.5 wt % aminomethylpropanol.

It has been found that the inclusion of the aminoalkylpropanol, especially the aminomethylpropanol, in the claimed depilatory compositions provides for a high degree of depilation but at a lower pH than is usual for conventional depilatory compositions. Typically depilatory compositions have a pH of about 12.5 at 20° C. One advantage of formulating products at lower pHs is that they are typically better tolerated by the skin.

vi) pH

The compositions of the invention have a pH in the range of from 10 to 12.5. It is preferred that the compositions have a pH in the range of from 10.2 to 12, more preferably from 10.3 to 11.8, such as 10.4 to 11.6, e.g. 10.5 to 11.5 and ideally 10.6 to 11.3, including all ranges in between these ranges. It has been found that the compositions of the invention can be formulated to pHs below 11, yet, still provide effective hair removal from an acceptable contact time. A pH range of 10.7 to 11.1 has been found to be especially preferred according to certain embodiments of the invention. It is therefore especially preferred that the compositions of the present invention have a pH of 11 or below.

In particular a pH in the range of from 10.4 to 11.6 and a contact time of from 2 to 7 minutes is preferred according to the invention, preferably a pH in the range of from 10.5 to 11.5 and a contact time of 2 to 7 minutes, more preferably a pH in the range of from 10.6 to 11.3 and a contact time of from 2 to 7 minutes is preferred. The pHs herein are those at 20° C.

vii) Optional Ingredients

The compositions of the invention may contain additional optional ingredients. Such optional ingredients may vary according to the physical format of the compositions and other formulation considerations.

The compositions may comprise components which accelerate the keratin degradation reaction in the hair such as urea, thiourea, dithioerythritol, dimethyl isosorbide (DMI), ethoxydiglycol (Transcutol®) or methyl propyl diol (MT diol). The compositions desirably comprise from 1 to 15 wt % of the accelerator based on the total weight of the composition, preferably from 2 to 13 wt %, such as 4 to 12 wt % and more preferably from 5 to 10 wt %. It is especially preferred that the compositions of the invention comprise urea as an accelerator, particularly in an amount of from 2, 3 or 5 wt % to 10 wt %, especially 6 to 9 wt %, such as up to 7 wt % or 8 wt %. It has been found that for a given composition the hair removal efficacy increases with an increasing concentration of accelerator, especially urea. However, the inclusion of urea in a composition can be associated with odours which consumers may find undesirable. Thus there is a need to produce compositions which are effective for hair removal but which do not exhibit an unacceptable level of malodour. Furthermore, the use of high concentrations of accelerators, such as urea, can cause the pH of the compositions to become unstable with time and to drift upwards to produce a more alkaline composition. This is undesirable as the more alkaline a composition is, the less it is well-tolerated by the skin. The above amounts have been found to provide a balance of efficacy and malodour control.

The compositions of the invention preferably comprise a gelling agent which can help to produce the desired rheological properties for the depilatory compositions of the invention. The inclusion of a gelling agent has also been found to aid the hair removal efficacy of the compositions and therefore gelling agents are especially preferred optional ingredients according to the present invention. Suitable gelling agents include acrylate based polymers, such as a carbomers. Other suitable gelling agents are alkyl vinyl ether/maleic anhydride copolymers such as methyl vinyl ether/maleic anhydride (PVM/MA) copolymer crosslinked with decadiene.

The inclusion of acrylate based polymers, and especially carbomers, is particularly preferred according to the present invention, especially in combination with urea, and even more preferably also with a gum such as xanthan gum.

The compositions of the invention may therefore also contain an acrylate based polymer, such as a carbomer. Suitable carbomers include the carbomers available under the tradename Carbopol™, available ex Lubrizol. Typically, if present, the carbomer is included in the composition in an amount of 0.25 to 5 wt %, such as 0.5 to 5 wt %, more preferably 0.75 to 4 wt %, preferably 1 to 3 wt %.

When a carbomer is present in the compositions of the invention, according to one aspect of the invention it has further been found to be advantageous if urea and/or a gum, especially Xanthan gum, is also present in the composition, particularly if the composition is a gel. The preferred amounts of the carbomer, urea and gum are as given hereinabove. The combination of the carbomer and the urea has been found to lead to enhanced hair removal results in the compositions of the invention and the effect has been found to be further enhanced by the inclusion of a gum, especially xanthan gum. Also it has been found that these combinations allow lower levels of the depilatory active and/or of the aminoalkylpropanol to be used, whilst maintaining efficacy of hair removal obtained from the use of the compositions An especially preferred option according to the present invention is the combination of a carbomer used in with urea and xanthan gum, with the amounts being as given herein. It has been found that the use of carbomers, compared to other gelling agents, provide depilatory compositions which show good efficacy but which can be formulated with lower amounts of accelerators, such as urea.

It has also been found that, surprisingly, the combination of certain accelerators, gelling agents, and gums can provide good hair removal results in depilatory compositions comprising a depilatory active even in the absence of an aminoalkylpropanol. It has been found that the combination of urea, a carbomer, especially a carbopol and a gum, especially xanthan gum as disclosed hereinabove provides this benefit.

It is preferred that the urea is included in the compositions in an amount of from 2, 3 or 5 wt % to 10 wt %, especially 6 to 9 wt %, such as up to 7 wt % or 8 wt %. The carbomer is typically included in the depilatory composition in an amount of 0.25 to 5 wt %, such as 0.5 to 5 wt %, more preferably 0.75 to 4 wt %, preferably 1 to 3 wt %. The gums, especially xanthan gum, are present in an amount of from 0.05 to 5 wt %, preferably 0.1 to 3 wt %, such as 0.1 to 0.5 wt % and most preferably 0.2 to 0.4% wt based on the total weight of the composition.

It has been found that when the compositions of the invention comprise carbopol (which has a pH of around 3 prior to neutralisation in-situ in the compositions), typically higher levels of an alkali, such as potassium hydroxide, are required to increase the pH of the compositions to a pH 10 to 12.5 and especially to above 10.5 compared to compositions which contain other gelling agents. It is acknowledged that the more alkali is present in the composition the greater is the potential for skin irritancy. However, it has been found that the amount of alkali to be added to the formulation, when AMP is used, can be kept relatively low. This allows the pH of the composition to be in the claimed range yet still provides a depilatory composition which is efficacious for hair removal. A depilatory composition with a pH of below 12 will be less irritating to skin than a composition with a pH of above 12; many commercial depilatory compositions have a pH of above 12, such as about 12.5. Also, it has been found that for compositions comprising AMP the amount of KOH added to the compositions can be kept relatively low, in particular for compositions having a pH up to about 11.5 whilst still providing effective depilatory effects.

As an alternative to the gelling agent, the compositions of the invention may contain viscosity increasing agent, especially a silica-based one, such as clay-based synthetic silicas. Suitable examples of silica-based viscosity increasing agents include Magnesium Aluminum Silicate, Magnesium Silicate, Magnesium Trisilicate, Lithium Magnesium Silicate, Lithium Magnesium Sodium Silicate and also clays such as montmorillonite, attapulgite, bentonite and hectorite. These materials are typically used in the compositions of the invention in an amount of from 0.1 wt % to 5 wt %, especially 0.5 wt % to 3 wt %, such as 0.75 wt % to 2 wt %. It has been found that a when a silica-based viscosity increasing agent is used, it is beneficial to also include an anionic acrylic polymer emulsion copolymer, such as one of the Aculyn polymers available from Dow Chemical in the compositions as this combination has been found to give good hair removal results. It has been found that amounts of the anionic acrylic polymer emulsion copolymer in the range 0.005 wt % to 1 wt % are preferred, such as 0.01 to 0.5 wt %, e.g. 0.02 wt % to 0.2 wt %.

It has also been found that good depilatory effects can be obtained by the inclusion of an alkyl vinyl ether/maleic anhydride copolymers, such as, methyl vinyl ether/maleic anhydride (PVM/MA) copolymer crosslinked with decadiene as a gelling agent. However typically it will be necessary to formulate such a composition with a higher concentration of an accelerator, such as urea, than would be necessary for a composition comprising a carbopol. The alkyl vinyl ether/maleic anhydride copolymers are typically present in an amount of 0.5 wt % to 5 wt %, such as 1 wt % to 3 wt %, more preferably 1.5 wt % to 2.5 wt %. These amounts of the alkyl vinyl ether/maleic anhydride copolymers are typically used with at least 5 wt % of accelerator, such as 5 wt % to 9 wt %, especially 7 wt % to 8.5 wt %. Urea is the preferred accelerator used with these copolymers.

According to one embodiment of the invention, the compositions of the invention may comprise a non-ionic surfactant, especially an alkyl polyglucoside surfactant, as these have been found to further improve the properties of the composition; it is believed that these ingredients aid the penetration of the depilatory actives into the hair. $C_6$ to $C_{14}$ alkyl polyglucosides are especially preferred, more particularly $C_8$ to $C_{12}$ alkyl polyglucosides, and especially $C_{10}$ alkyl polyglucoside (also known as cocoglucoside). Such ingredients are preferably present in an amount of from 0.1 to 5 wt % based on the total weight of the composition, preferably 0.15 to 2.5 wt %, such as 0.2 to 1.5 wt %, e.g. 0.2 to 1 wt %. It is especially preferred that the compositions comprise cocoglucoside in the aforementioned amounts. However non-ionic surfactants are not necessarily required in all types of compositions according to the invention.

In another embodiment of the invention the compositions may comprise a film former, such as a methacrylate based copolymer, to improve water resistance of compositions. One such suitable methacrylate based copolymer is dimethylacrylamide/acrylic acid polystyrene ethyl methacrylate copolymer which is available commercially under the tradename Invisaskin™ RB ex Grant Industries. If present the methacrylate based copolymer is preferably included in an amount of from 0.001 to 0.5 wt %, such as 0.01 to 0.2 wt %, e.g. 0.02 to 0.1 wt %. Film former ingredients will not necessarily be included in all types of compositions according to the invention. Typically they will be included in compositions which dry to a film upon use.

Thus according to certain embodiments of the invention it is preferred that the compositions comprise an alkyl polyglucoside surfactant and a methacrylate based copolymer. A preferred combination for use in the compositions of the invention is cocoglucoside and dimethylacrylamide/acrylic acid polystyrene ethyl methacrylate copolymer, especially in the amounts as stated above. It is preferred that according to one aspect of the invention, the compositions of the invention comprise potassium thioglycolate and/or thioglycolic acid, potassium hydroxide, aminomethylpropanol, an alkyl polyglucoside and/or a methacrylate based copolymer.

According to one aspect of the invention, depilatory compositions comprising the following are provided:
- 0.5 to 10 wt % potassium thioglycolate and/or thioglycolic acid,
- 0.5 to 5 wt % potassium hydroxide,
- 0.2 to 10 wt % aminomethylpropanol
- 0.1 to 1.5 wt % alkyl polyglucoside and/or
- 0.001 to 0.2 wt % methacrylate based copolymer based on the total weight of the composition.

According to a preferred aspect of the invention, depilatory compositions comprising the following are provided:
- 0.5 to 10 wt % potassium thioglycolate and/or thioglycolic acid,
- 0.5 to 5 wt % potassium hydroxide,
- 0.2 to 10 wt % aminomethylpropanol,
- 5 to 10 wt % urea.

According to a preferred aspect of the invention, depilatory compositions comprising the following are provided:
- 0.5 to 10 wt % potassium thioglycolate and/or thioglycolic acid,
- 0.5 to 5 wt % potassium hydroxide,
- 0.2 to 10 wt % aminomethylpropanol,
- 0.5 to 5 wt % carbomer.

According to another preferred aspect of the invention, depilatory compositions comprising the following are provided:
- 0.5 to 10 wt % potassium thioglycolate and/or thioglycolic acid,
- 0.5 to 5 wt % potassium hydroxide,
- 0.2 to 10 wt % aminomethylpropanol,
- 0.1 to 0.5 wt % of a gum, especially xanthan gum.

It is especially preferred that the depilatory compositions comprise:
- 0.5 to 10 wt % potassium thioglycolate and/or thioglycolic acid,
- 0.5 to 5 wt % potassium hydroxide,
- 0.2 to 10 wt % aminomethylpropanol,
- 5 to 10 wt % urea,
- 0.5 to 5 wt % carbomer,
- 0.1 to 0.5 wt % of a gum, especially xanthan gum.

The depilatory composition of the present invention may comprise water depending upon the physical form of the composition. However gels, mousses foams, creams and lotions will typically comprise higher amounts of water than will a peelable film composition. Thus the compositions of the invention may be aqueous based. In gel, mousse, foam, cream and lotion compositions the amount of water present in the compositions is preferably at least 40 wt %, more usually at least 50 wt %, more preferably at least 60 wt % or 65 wt % based on the total weight of the composition. Gel compositions comprising the aforementioned amounts of water have been found to be particularly effective according to the present invention. Peelable gel compositions typically comprise 40 to 75 wt % water, more preferably 45 to 70 wt %, such as 50 to 60 wt % water.

The depilatory compositions may further include a humectant. Suitable humectants include polyols, such as glycerine, propylene glycol and butylene glycol. Glycerine is preferred. The humectant may be present in an amount of from 0.05 to 10 wt %, preferably 0.25 to 5 wt %, such as 0.5 to 3 wt %.

The compositions of the invention may also comprise a chelating agent. Any suitable chelating agent may be used and a preferred chelating agent is sodium gluconate. Conventional amounts may be used for example 0.01 wt % to 2 wt %.

The compositions may contain fragrances and/or colouring agents in conventional amounts.

Depending upon the physical form of the composition, the composition may also contain one or more thickening agents such as one or more gums. Any suitable thickening gum may be used, such as xanthan gum which is especially preferred, particularly when used in combination with a carbomer gelling agent and urea as an accelerant. Typically, when included, the gums are present in an amount of from 0.05 to 5 wt %, preferably 0.1 to 3 wt %, such as 0.1 to 0.5 wt % and most preferably 0.2 to 0.4% wt based on the total weight of the composition. Such thickeners are typically used in gel compositions of the invention.

If desired the depilatory compositions may further include an emollient such as an oil or a wax, especially in a cream or lotion composition. A preferred oil emollient is mineral oil. A preferred wax emollient is ceteareth-20. The compositions may include a mixture of an oil and a wax as a combined emollient. The oil emollient and/or the wax emollient may be included in conventional amounts.

Other components which may be incorporated into the depilatory compositions include a buffer such as sodium silicate or magnesium silicate. The depilatory composition may further comprises other salts selected from di- and tri-valent salts, such as magnesium chloride, calcium chloride ammonium chloride, magnesium sulphate, calcium sulphate, aluminium sulphate, magnesium carbonate, calcium sulphate, calcium carbonate. A preferred salt is magnesium chloride. In an alternative embodiment the composition can comprise a salt extract, such as dead-sea salts. Such salts may be included in conventional amounts.

The present invention also provides a method of removing hair from a bodily surface of a mammal, such as the head, body or face, by;
i) applying a composition according to the invention to a bodily surface of the mammal, from where it is desired to remove hair,
ii) allowing the composition to contact the bodily surface for a period of time of from 1 to 10 minutes,
iii) and subsequently removing the composition from the bodily surface.

The compositions of the invention may be applied and removed by any suitable method according to the type of composition. Such methods are well known in the art. For example, a gel, cream or lotion may be applied to the area to be treated either by hand or with the aid of a device (such as a spatula, roll-on, tube applicator or similar device). Mousse or foam compositions may be applied directly from a dispensing device such as an aerosol can or pump dispenser. Typically, peelable films are applied as a gel or liquid composition and dry to form a film which is then peeled off at the end of the desired contact time.

After the required contact time between the unwanted hairs and the depilatory composition of the invention has elapsed and the unwanted hairs have been degraded, the depilatory composition and the degraded hairs may be removed by any suitable means, for example, in the same way as in which the composition was applied. Typically a spatula or similar device especially one with a substantially straight edge, or a flexible object such as a foam/tissue/cloth/wipe type object may be used to remove the depilatory composition and the degraded hairs. This is achieved simply by moving the spatula etc. or flexible object around the area to which the depilatory composition has been applied in order to 'scoop' up the same. In this way the depilatory composition is lifted from the area to which it has been applied and can be removed. Any residual composition may be removed by, for example, rinsing with water. Alternatively the composition may be rinsed away with water.

The depilatory compositions of the invention are typically allowed to contact the bodily surface, e.g. skin or hair, for at least 2 minutes, preferably at least 3 minutes, such as 4 minutes. However in order to reduce any potential skin irritation from the use of the compositions of the invention it is preferred that the contact time is 9 minutes or less, preferably 8 minutes or less, such as 7 minutes or less. Preferred contact times for the compositions of the invention and the hair to be removed are in the range of from 2 to 8 minutes, more preferably 3 to 7 minutes, such as 4 to 7 minutes (including ranges there-between). It has been found that the compositions of the invention provide effective hair removal yet are well tolerated by the skin, when these contact times are used.

Also provided according to the present invention is a method of producing a composition according to the invention which comprises the step of the addition of the aminoalkylpropanol to a composition comprising a depilatory active and an alkali metal hydroxide. It has been found that for some types of compositions according the invention, such as gels, the addition of the aminoalkylpropanol, can thicken the composition too much and make subsequent production and processing difficult. It has been found that by adding the aminoalkylpropanol in this manner this tendency to thicken the compositions can be minimised and thus production and subsequent processing is made easier.

One preferred method for producing gel compositions according to the present invention is;
- to 80 wt % of the total amount of added water in the composition sprinkle on top the carbomer (when present) and allow to stand for 60-90 minutes, then stir. A gel is produced onto which the gum thickener (e.g. xanthan gum) is sprinkled and after approximately 5 minutes the composition is stirred. This produces premix A.
- to the remaining 20 wt % of the added water add the accelerator (e.g. urea) and stir until homogeneous. This produces premix B.
- Mix together premix A and B and stir.
- To the resulting mixture and the remaining ingredients except for the depilatory active, alkali metal hydroxide and the aminoalkylpropanol (e.g. sodium gluconate, glycerine, stir and add the perfume).
- To this mixture add the alkali metal hydroxide (e.g. potassium hydroxide) and the depilatory active (e.g. potassium thioglycolate) and stir.
- Finally stir in the aminoalkylpropanol (e.g. aminomethylpropanol to produce the gel composition.

Ideally depilatory compositions will remove as high a percentage as possible of unwanted hair in a single treatment. As the application method can very slightly with the user (both in terms of hair type treated, application method, contact time and personal levels of expectation etc.) it is generally considered that hair removal results above about 50% would be considered as acceptable by the user. Results higher than this are preferred such as at least 70%, or even more preferably at least 80% and ideally above 90%.

The use of the gelling agents, urea and gums, especially carbomers (most especially carbopols), urea and xanthan gum in depilatory compositions comprising a depilatory active has been found to be especially effective in compositions comprising an aminoalkylpropanol, such as aminomethylpropanol. However it has also been found that this combination can provide good hair removal efficacy in other types of compositions too.

The depilatory active can be any of the types described above, especially the compositions comprising a thiol group. The depilatory compositions may further comprise an alkali metal hydroxide selected from sodium hydroxide and/or potassium hydroxide.

For the avoidance of doubt, it is to be understood that the types and amounts of the depilatory active, urea, carbomer (especially carbopol), the gums (especially xanthan gum) and the alkali metal hydroxide as disclosed herein for the other aspects of the invention apply equally here, mutatis mutandis. It is also to be understood that the depilatory compositions of this aspect of the invention may be of any of the physical forms disclosed herein and that any of the optional ingredients disclosed herein may be included in the depilatory compositions of this aspect.

Thus, there is also according to a further embodiment of the invention depilatory compositions comprising a depilatory active (as described above and especially containing a thiol group), urea, a carbomer (especially a carbopol) and a gum, especially xanthan gum. These compositions have been found to exhibit good hair removal results. These compositions do not necessarily need to comprise an aminoalkylpropanol, such as aminomethylpropanol, and in some embodiments of the invention aminoalkylpropanols are not included in the formulations. Thus according to one aspect of the invention, depilatory compositions are provided which comprise a depilatory active, urea, a carbomer, especially a carbopol and a gum, especially xanthan gum, but which do not comprise an aminoalkylpropanol, such as aminomethylpropanol.

Therefore, according to a further aspect of the invention, there is also provided the use of a combination of urea, carbomer, especially a carbopol, and a gum, especially xanthan gum, to provide for efficacious hair removal in depilatory compositions comprising a depilatory active. Also provided is the use of a combination of urea, carbomer, especially a carbopol, and a gum, especially xanthan gum, to prepare a depilatory composition comprising a depilatory active.

The compositions of the invention which are formulated with the combination of urea, carbomer and a gum but without the inclusion of the aminoalkylpropanol, also provide a high degree of depilation but typically at a higher pH than if the aminoalkylpropanol, had been included. This may be desirable for some depilatory compositions and also provides for different types of effective compositions to be provided.

The invention will now be described in more detail with reference to the following non-limiting examples. Further examples within the scope of the present invention will be apparent to the person skilled in the art.

EXAMPLES

Examples 1 and 2: Gel Compositions

Two examples of gel compositions according to the present invention are given in Table 1 below. The amounts given are as the raw material ingredient used to make the composition. Unless otherwise stated the ingredients were used as 10000 active ingredients.

TABLE 1

Gel compositions according to the present invention.

| Ingredients | Example 1 % wt/wt | Example 2 % wt/wt |
|---|---|---|
| Potassium thioglycolate*[1] | 10.0 | 10.0 |
| Potassium hydroxide*[2] | 4.1 | 4.1 |
| Aminomethylpropanol*[3] | 3.0 | 3.0 |
| Xanthan gum | 0.4 | 0.4 |
| Urea | 8.0 | 8.0 |
| Glycerin | 1.0 | 1.0 |
| Sodium gluconate | 0.1 | 0.1 |
| Perfume | 0.4 | 0.4 |
| $C_{10-30}$ alkyl acrylate crosspolymer*[4] | 1.4 | 1.4 |
| Methacrylate based co-polymer*[5] | — | 2.0 |
| $C_{10}$ polyglucoside (cocoglucoside) *[6] | — | 1.0 |
| Deionised water | balance | balance |

*[1] a 44% active solution of potassium thioglycolate was used, so active concentration is 4.4 wt % in the composition.
*[2] a 50% active solution of potassium hydroxide was used, so active concentration is 2.05 wt % in the composition.
*[3] a 99% active aminomethylpropanol raw material was used, so active concentration is 2.97 wt % in the composition.
*[4] a carbomer commercially available as Carbopol$^{RTM}$ Ultrez 20, ex Lubrizol; an acrylates C10-30 alkyl acrylate crosspolymer.
*[5] a 2-3 wt % solution of dimethylacrylamide/acrylic acid polystyrene ethyl methacrylate copolymer based composition, also containing water, rice bran extract, sodium benzoate and phenoxyethanol, available commercially as Invisaskin$^{RTM}$ ex Grant Industries.
*[6] cocoglucoside, commercially available as a 50 wt % solution as Plantacare$^{RTM}$ 818 UP ex BASF.

The gel compositions were translucent. They were made by the preferred method described hereinabove using premix A and premix B which are mixed together, with the potassium hydroxide, and the potassium thioglycolate added to this mixture. Finally the aminomethylpropanol was added to produce the gel composition.

The results obtained with Examples 1 and 2 are given in Table 2.

TABLE 2

Example 1 and 2 results

| | Example 1 | Example 2 |
|---|---|---|
| Initial pH at 20° C. | 10.75 | 10.88 |
| pH on storage @ 30° C. 1 week, 2 weeks and 4 weeks storage | 10.601 (1 week) 10.504 (2 weeks) 10.709 (4 weeks) | 10.583 (1 week) 10.618 (2 weeks) 10.693 (4 weeks) |
| Hair removal results on hair of at least 2 mm length on lower legs | 92.47% | — |

Hair Removal Test

Example 1 was tested for hair removal efficacy by the following test:
1. Fifteen female panellists with hair length of at least 2 mm on their lower legs who have never had an adverse event from depilatory creams or gels were recruited.
2. Panellists are asked if they have ever previously used depilatory cream and if this has ever caused any irritation, this data is recorded.
3. There are 6 tests areas on each panellist:
    Test area 1: Along the shin bone just below the knee, left leg
    Test area 2: Along the shin bone just below the knee, right leg
    Test area 3: Outside edge of calf, half way between knee & ankle, left leg.
    Test area 4: Outside edge of calf, half way between knee & ankle, right leg.
    Test area 5: Along the shin bone just above the ankle, left leg.
    Test area 6: Along the shin bone just above the ankle, right leg.
4. Prior to applying the product, the test areas are marked out on the panellist's legs using a 10×5 cm template which is placed on the panellist's legs in the portrait orientation (a suitable mark is made on the legs to enable accurate replacement) and a hair count taken.
5. The depilatory product is then applied using the following 5 minute method:
    the product is applied completely covering the test area with a thick, even layer of depilatory product using the spatula provided. The timer for 6.5 minutes is started as soon as product starts to be applied; 5 minutes to represent the application time of the product and a further 1.5 minutes to represent the time it would take on average for a consumer to apply product to the whole of both their lower legs. After 6.5 minutes the product is removed from the leg using the spatula.
6. The leg is then rinsed thoroughly and dried.
7. The grid is repositioned over the leg referring to the markers and a second hair count is taken.

As a comparison against Example 1, a commercially available hair removal product (NAIR® Glide on Depilatory product, having a pH at 20° C. of around 12.5) was also tested by the same method as above. The results are given in Table 3.

TABLE 3 hair removal results

| Example | % hair removal achieved |
|---|---|
| NAIR$^{RTM}$ Glide on Depilatory product | 86.13% |
| Example 1 | 92.47% |

The compositions of the invention are well tolerated by the skin yet provide effective hair removal in an acceptable contact time with the hair to be removed, even though the pH of the compositions is relatively low compared to typical depilatory compositions comprising depilatory actives such as the Nair® Glide on Depilatory product. They also exhibit good pH stability on storage.

Example 3—Cream Formulation

A cream formulation according to the present invention was prepared according to the formulation in Table 4. The composition was made by the following method and had a pH at 20° C. of 10.5.

A first phase (A) was prepared by weighing out 80% of total amount of D.I. water into a main vessel and adding the talc, magnesium trisilicate and sodium gluconate with stirring. The resulting composition was heated in a water bath to 75° C.

A second phase (B) was prepared by making a mixture of the glycerine, sorbitol and xanthan gum. The mixture was stirred to make a paste which was then heated to in a water bath.

An oil phase (C) was prepared by weighing the cetearyl alcohol, ceteareth 20 and thick mineral oil into a beaker, stirring the mixture and heating it in the water bath to 75° C. The mixture was stirred as required.

Once all the phases A, B, and C had reached 75° C., the oil phase (C) was stirred and at the same time phase B was stirred into phase A and homogenised for 1 minute to form an homogenous mixture and then phase C was added and the homogenisation continued for a further 3 minutes.

The resulting homogenised mixture of A, B and C was left to cool at ambient temperature until it reached 50° C.

A urea containing phase (D) was prepared by adding the remaining 20% of the D.I. water into a vessel, and then stirring to form a vortex. The urea was added to the vortex in portions to allow time for each portion to dissolve. Once all the urea has dissolved the lithium magnesium sodium silicate was added into the vortex followed by the acrylates polymer.

When the mixture of phases A, B and C had cooled to 50° C. the urea phase (D) was added to the mixture with stirring to produce a homogenous cream. The stirring rate was reduced to a slow rate and the mixture was allowed to cool to 30° C. when the fragrance was added to the mixture whilst it was being stirred.

The TGK, potassium hydroxide and aminomethylpropanol were then added with stirring and the composition was then homogenised for about 4 minutes to produce a homogenous smooth cream.

TABLE 4

Cream formulation

| Ingredients | Example 3 (% wt) |
| --- | --- |
| D.I. water | 61.34 |
| Cetearyl Alcohol | 4.40 |
| Ceteareth 20 | 1.76 |
| Glycerin | 1.00 |
| Sodium Gluconate | 0.10 |
| Magnesium Trisilicate | 0.50 |
| Urea | 3.00 |
| Anionic acrylic polymer emulsion Copolymer*[7] | 0.10 |
| Potassium Thioglycolate (TGK) 43.1-44.5% solution | 12.90 |
| Thick Mineral Oil | 4.80 |
| Lithium Magnesium Sodium Silicate*[8] | 0.20 |
| Talc | 2.00 |
| Sorbitol | 1.00 |
| Perfume | 0.40 |
| Aminomethylpropanol | 4.00 |
| Potassium Hydroxide 50% | 2.50 |
| Total | 100.00 |

*[7]Aculyn 33 polymer, ex Dow Chemicals, 28% active ingredient so the active concentration is 0.028% in the composition.
*[8]Laponite XLG, ex BYK Additives, 100% active ingredient.

Example 4—the Effect of Aminomethylpropanol on Hair Removal Efficacy

The following depilatory compositions in Table 5 were prepared by the method detailed below.

The carbopol was sprinkled onto the surface of 80% of the total amount of D.I. water in the compositions and was left to stand for about 45 minutes until all the carbopol had wet into the water.

After that time a paddle stirrer was used to mix the liquid from the previous stage until a lump-free mixture was obtained.

Separately the urea was dissolved in the remaining 20% of the total amount of D.I. water.

The urea solution was added to the carbopol/water mixture, followed by the sodium gluconate and glycerin and the mixture was stirred until the ingredients had mixed in and a gel had been produced.

The stirring was stopped and the xanthan gum was sprinkled in the surface of the gel and left for 15 minutes to wet into the gel.

Once the xanthan gum was wet into the mixture, the fragrance was added with stirring.

Finally the aminomethylpropanol, or TRIS or TEA was added together to the mixture with the potassium hydroxide and the TGK to produce the final gel composition.

TABLE 5 compositions containing aminomethylpropanol or other amines

| Ingredients | Ex 4a (% wt) | Ex 4b (% wt) | Ex 4c (% wt) comparative | Ex 4d (% wt) comparative |
| --- | --- | --- | --- | --- |
| Xanthan gum | 0.200 | 0.20 | 0.30 | 0.30 |
| Urea | 8.00 | 8.00 | 8.00 | 8.00 |
| Sodium gluconate | 0.10 | 0.10 | 0.10 | 0.10 |
| Acrylates Copolymer*[4] | 1.40 | 1.40 | 1.40 | 1.40 |
| Perfume | 0.40 | 0.40 | 0.40 | 0.40 |
| D.I. water | 71.80 | 68.41 | 70.70 | 70.80 |
| Potassium Hydroxide 50% soln*[2] | 4.10 | 4.85 | 5.10 | 5.00 |
| Potassium Thioglycolate (TGK) 44.5% solution*[1] | 10.00 | 12.90 | 10.00 | 10.00 |
| Aminomethylpropanol*[3] | 3.00 | 3.00 | — | — |
| TRIS*[9] | — | — | 3.00 | — |
| TEA*[10] | — | — | — | 3.00 |
| Glycerin | 1.00 | 1.00 | 1.00 | 1.00 |
| Total | 100.0 | 100.0 | 100.0 | 100.0 |
| pH at 20° C. | 10.80 | 10.75 | 10.96 | 10.94 |

*[1]a 44.5% active solution of potassium thioglycolate was used, so active concentration is 5.74 wt % or 4.45 wt % as applicable.
*[2]a 50% active solution of potassium hydroxide was used, so active concentrations are 2.05 wt %, 2.42 wt %, 2.55 wt % and 2.5 wt % respectively in the compositions.
*[3]a 95.5% active aminomethylpropanol raw material was used, so active concentration is 2.86 wt % in the composition.
*[4]as in Example 1 and 2.
*[9]TRIS was used as Ultra PC, ex Angus Chemicals, a 99% active solution so the active concentration is 2.97 wt %.
*[10]TEA was used as a 99% active solution (ex-Dow Chemicals) so the active concentration is 2.97 wt %.

Examples 4a and 4b comprise aminomethylpropanol and are according to the invention. Example 4c is a comparative example which comprises TRIS (tris(hydroxymethyl)aminomethane) and Example 4d is a comparative example which comprises TEA (triethanolamine).

The first AMP containing composition (Example 4a) contained 10.00 wt % of the TGK solution to match the amount of TGK present in the comparative examples 4c and 4d. The second AMP containing composition (Example 4b) contained 12.90 wt % of the TGK solution to match the typical level of depilatory active commonly used in depilatory creams for normal skin types.

The above compositions were tested to assess their hair removal efficacy following the test method given above. The hair removal results are given in Table 6 below.

TABLE 6 hair removal test results

| Example | % hair removal achieved |
| --- | --- |
| 4a, contains AMP | 93.21% |
| 4b, contains AMP | 94.93% |
| 4c, contains TRIS, no AMP | 63.57% |
| 4d, contains TEA, no AMP | 57.36% |

The p-value was 0.0001 which indicates significant differences between the examples at a 95% confidence level.

The above hair removal results demonstrate the advantages of including AMP in the depilatory compositions as the compositions of examples 4a and 4b demonstrate significantly higher percentage hair removal than the compositions of examples 4c or 4d which do not contain AMP but instead contain other amine-based ingredients.

Example 5—Hair Removal Efficacy on Storage

Example 4a comprising AMP, example 4c comprising TRIS and example 4d comprising TEA were tested for their hair removal efficacy, using the above method, after preparation. The examples were then stored at room temperature for a period of 3 months. At 1 month and 2 month storage times, a sample of the stored example was removed and tested for hair removal efficacy using an in-vitro hair removal test model. The examples were also tested at the end of their 3 month storage period. The results of the hair removal testing is given below in Table 7.

The in-vitro test method used was:
A sheet containing a series of regularly spaced holes is incubated in an oven at 32° C. for 30 minutes.
30 hair samples 3-4 cm in length (virgin hair, chemically untreated, purchased from Hugo Royer International Limited) were threaded through opposing holes in a sheet in groups of 5 hairs and sealed into place with tape on the back of the sheet having a guard at the end of the sheet.
The hairs are then trimmed to approximatively 0.6 cm in length (the height of the lane guards).
Approximately 30 g of the depilatory composition to be tested was applied to the hairs in an even layer covering all the hairs using a spatula.
The sheet is then incubated in an oven at 32° C. for 10 minutes.
The hairs are then removed from the sheet by holding the spatula (which has been weighted with a weight of about 250 grams) between finger and thumb at the thin end and scraping in a forward direction across the surface of the sheet, taking care to maintain a steady angle during scraping and apply constant pressure throughout scraping.
The number of hairs removed per scrape is recorded.
The experiment was repeated 4 times.
Results are expressed in terms Oo Hair removal (0% HR) per scrape;

% Hair Removal=(hairs removed/hairs initially)×100

TABLE 7 hair removal test results after storage

| Example | 0 months | 1 month | 2 months | 3 months |
|---|---|---|---|---|
| | % hair removal | | | |
| 4a, contains AMP | 94.4% | 88.9% | 96.7% | 75.6% |
| 4c, contains TRIS, no AMP | 85.6% | 42.2% | 46.7% | 48.9% |
| 4d, contains TEA, no AMP | 86.7% | 83.3% | 92.2% | 60.0% |
| | pH at 20° C. | | | |
| 4a, contains AMP | 10.92 | 10.80 | 10.58 | Not tested |
| 4c, contains TRIS, no AMP | 10.55 | 10.40 | 10.31 | 10.23 |
| 4d, contains TEA, no AMP | 10.56 | 10.39 | 10.28 | 10.53 |

The above results demonstrate that the AMP containing compositions of the present invention still provide the highest percentage of hair removal even after being stored for 3 months. This is believed to be related to the pH stability of the compositions according to the invention.

Example 6—pH and Hair Removal Results

Examples 4a and 4b, which are examples according to the invention, gave hair removal results of 93.21% and 94.92% respectively when tested as in Example 4 (see table 5). These compositions had a pH of 10.8 and 10.75 at 20° C. The compositions provided for good hair removal results and were well tolerated by the skin.

A comparative, commercially, available depilatory composition Veet Depilatory Cream (normal skin type) which is not according to the present invention (as it does not contain AMP) was also tested according to the method given above to determine its hair removal properties. This composition had a pH of 12.6 at 20° C. The composition exhibited a hair removal result of 97.6%.

The hair removal results achieved for Examples 4a and 4b and the commercial, comparative formulation are similar. However the lower pH of Examples 4a and 4b is considered to be preferable for a depilatory composition as there is understood to be a reduced likelihood of damage to the skin during or after usage of the product, particularly if the usage instructions are not correctly followed and the product is left in contact with the skin for longer than the recommended treatment time.

Example 7—the Effect of Carbopol and Urea on Hair Removal Efficacy

Gel compositions according to the present invention were prepared according to the formulations given in Table 8. Compositions 7a and 7b were prepared by the method given for Example 4. For compositions 7c and 7d comprising the PVM/MA Decadiene crosspolymer, the following method was used to produce the compositions.

A first phase (A) was produced by adding 80% of the total amount of the D.I. water to a beaker, then adding the PVM/MA Decadiene crosspolymer and homogenising the resulting mixture.
The Glycerin was added to the above mixture and the resultant mixture homogenised again.
A second phase (B) was produced by mixing the urea with the remaining 20% of the D.I. water.
The second phase (B) was added to the first phase (A) mixture followed by the magnesium chloride and the sodium gluconate. The resulting mixture was homogenised to produce a homogeneous composition.
The fragrance was added to the above mixture which was then re-homogenised.
The aminomethylpropanol was added followed by the potassium chloride and KOH with the composition being stirred well with a paddle stirrer after each ingredient was added.

TABLE 8

Gel compositions according to the present invention

| Ingredients | Ex 7a (% wt) | Ex 7b (% wt) | Ex 7c (% wt) | Ex 7d (% wt) |
|---|---|---|---|---|
| Xanthan gum | 0.2 | 0.3 | — | — |
| Urea | 8.0 | 3.0 | 8.0 | 3.0 |
| Acrylates Copolymer*[4] | 1.4 | 1.4 | — | — |
| PVM/MA Decadiene crosspolymer *[11] | — | — | 2.0 | 2.0 |
| Sodium Gluconate | 0.1 | 0.1 | 0.1 | 0.1 |
| Perfume | 0.4 | 0.4 | 0.4 | 0.4 |
| D.I. water | 71.8 | 76.7 | 68.0 | 73.0 |
| Potassium Hydroxide 50% soln*[2] | 4.1 | 4.1 | 2.5 | 2.5 |
| Potassium Thioglycolate (TGK) 44.5% solution*[1] | 10.0 | 10.0 | 12.9 | 12.9 |

TABLE 8-continued

Gel compositions according to the present invention

| Ingredients | Ex 7a (% wt) | Ex 7b (% wt) | Ex 7c (% wt) | Ex 7d (% wt) |
|---|---|---|---|---|
| Aminomethylpropanol*3 | 3.0 | 3.0 | 5.0 | 5.0 |
| Glycerin | 1.0 | 1.0 | 12.9 | 12.9 |
| Magnesium chloride | — | — | 0.1 | 0.1 |
| Total | 100.0 | 100.0 | 100.0 | 100.0 |
| pH at 20° C. | 10.67 | 10.73 | 10.42 | 10.32 |

*1 a 44% active solution of potassium thioglycolate was used, so active concentration is 4.4 wt % and 5.7 wt % respectively in the compositions.
*2 a 50% active solution of potassium hydroxide was used, so active concentration is 2.05 wt % or 1.25 wt % as appropriate.
*3 a 95.5% active aminomethylpropanol raw material was used, so active concentration is 2.86 wt % and 4.77 wt % in the composition respectively. The aminomethylpropanol used was AMP Ultra PC 2000, ex Angus Chemical Company.
*4 as in Example 1 and 2.
*11 Stabileze QM, a 90% active product of methyl vinyl ether/maleic anhydride (PVM/MA) copolymer crosslinked with decadiene in 10% water, ex-IS, so active concentration is 1.8 wt %.

The compositions of Examples 7a to 7d were tested to determine their efficacy for hair removal by following the method given hereinabove. The results of the hair testing are shown in the Table 9 below:

TABLE 9 the efficacy of compositions 7a to 7d on hair removal

| | Hair removal results | | | |
|---|---|---|---|---|
| | Ex 7a Carbopol 8 wt % urea | Ex 7b Carbopol 3 wt % urea | Ex 7c Stabileze 8 wt % urea | Ex 7d Stabileze 3 wt % urea |
| % hair removal | 84.38 | 53.94 | 71.75 | 34.45 |

From the above results it can be seen that the Carbopol gelling agent gives better hair removal results (for a given percentage of urea in the formulation) than does the PVM/MA Decadiene crosspolymer (Stabilize) gelling agent. Therefore, Carbopols are especially preferred gelling agents according to the present invention, and compositions comprising Carbopol, urea and xanthan gums are especially preferred.

The PVM/MA Decadiene crosspolymer (Stabileze) gelling agent provides acceptable levels of hair removal provided that a sufficient amount of urea is also included in the composition. The amount of urea required for the Stabileze compositions to obtain a highly effective depilatory composition has been found to be higher than for an equivalent Carbopol containing formulation.

It can also be seen from the above results that the formulations containing Carbopol, urea and xanthan gum (7a and 7b) provide for more effective hair removal than their equivalent formulations containing PVM/MA Decadiene crosspolymer (Stabileze) and urea (7c and 7d) even though the Carbopol, urea and xanthan gum containing formulations contain less depilatory active (TGK) and aminomethylpropanol). This demonstrates that the combination of Carbopol, urea and Xanthan gum allows for a reduction in the amount of depilatory active and aminomethylpropanol used in the compositions whilst still achieving enhanced hair removal results compared to the compositions comprising PVM/MA Decadiene crosspolymer (Stabileze) and urea.

Example 8—Further Examples According to the Invention

Gel compositions according to the present invention were prepared according to the formulations given in Table 10. The compositions were prepared by the method below.

A first phase (A) was prepared by weighing out 80% of the total amount of the D.I. water into a main vessel and adding the sodium gluconate with stirring. The resulting composition was heated in a water bath to 75° C.

A second phase (B) was prepared by making a mixture of the glycerine and xanthan gum. The mixture was stirred to make a paste and this paste was added to the first phase (A).

The mixture of phases A/B was homogenised for about 30 seconds to produce a smooth gel and this was placed in a water bath to heat to 75° C.

An oil phase (C) was prepared by weighing the cetearyl alcohol, ceteareth 20 and paraffin oil into a beaker, stirring the mixture and heating it in the water bath to 75° C. The mixture was stirred as required.

Once all the phases A/B, and C had reached 75° C., the oil phase (C) was stirred and added to the A/B phase and homognised for 3 minutes to produce a smooth emulsion.

The resulting homogenised mixture of A, B and C was left to cool at ambient temperature, with stirring until the mixture reached 50° C.

A urea containing phase (D) was prepared by adding the remaining 20% of the total amount of the D.I. water into a vessel, and then stirring to form a vortex. The carbopol or Lithium Magnesium Sodium Silicate was slowly sprinkled into the vortex and left to wet out (about 10 minutes). The urea was added to the vortex and the composition was stirred for about 10 minutes to allow the urea to wet fully.

When the mixture of phases A, B and C had cooled to 50° C. the urea phase (D) was added to the mixture and the resultant mixture was homogenised followed by stirring using a paddle stirrer for which the stirring rate was reduced to a slow rate and the mixture was allowed to cool to 30° C.

The TGK was added, followed by the aminomethylpropanol.

This mixture was homogenised to produce a smooth, uniform, cream which was then allowed to cool to 30° C. again at which point the potassium hydroxide in an amount sufficient to produce the pH detailed for the compositions.

Finally, the compositions were homogenised for around 30 seconds to 1 minute to ensure uniformity.

TABLE 10

Gel compositions according to the present invention

| Ingredients | Ex 8a (% wt) | Ex 8b (%wt) |
|---|---|---|
| Xanthan gum FN | 0.8 | 0.8 |
| Urea | 8.0 | 8.0 |
| Acrylates Copolymer*4 | 1.0 | — |
| Lithium Magnesium Sodium Silicate*8 | — | 1.0 |
| Sodium Gluconate | 0.1 | 0.1 |
| Paraffin oil | 5.0 | 5.0 |
| Potassium Hydroxide 50% soln*2 | 5.32 | 3.85 |
| Potassium Thioglycolate (TGK) 44.5% solution*1 | 10.0 | 10.0 |
| Aminomethylpropanol*3 | 3.0 | 3.0 |
| Ceteareth 20 | 0.4 | 0.4 |
| Cetearyl alcohol | 3.5 | 3.5 |

TABLE 10-continued

Gel compositions according to the present invention

| Ingredients | Ex 8a (% wt) | Ex 8b (%wt) |
|---|---|---|
| Glycerin | 5.0 | 5.0 |
| D.I. water | to 100.0 | to 100.0 |
| pH at 20° C. | 11.597 | 11.590 |

*[1] a 44% active solution of potassium thioglycolate was used, so active concentration is 4.4 wt % in the composition.
*[2] a 50% active solution of potassium hydroxide was used, so active concentration is 2.66 wt % or 1.92 wt % respectively.
*[3] a 95.5% active aminomethylpropanol raw material was used, so active concentration is 2.86 wt % and 4.77 wt % in the composition respectively. The aminomethylpropanol used was AMP Ultra PC 2000, ex Angus Chemical Company.
*[4] as for Example 1 and 2.
*[8] Laponite XLG, ex BYK Additives, 100% active ingredient.

The Ceteareth 20 used was Emulgin B2 ex BASF, a 100% active ingredient.

The Cetearyl alcohol used was Lanette S3 Past ex BASF, a 100% active ingredient.

The compositions of Examples 8a and 8b were tested to determine their efficacy for hair removal by following the method given hereinabove. The results of the hair testing are shown in Table 11 below:

TABLE 11 the efficacy of compositions 8a and 8b on hair removal

| | Hair removal results | |
|---|---|---|
| | Ex 8a | Ex 8b |
| Preferred optional ingredients | Carbopol, urea, xanthan gum | Lithium Magnesium Sodium Silicate, urea, xanthan gum |
| % hair removal | 70.0 | 63.3 |

The above results demonstrate that the Laponite-containing composition provides for acceptable hair removal but the carbopol-containing composition provides for a greater degree of hair removal. Compositions comprising carbopol are preferred according to the invention.

Example 9—the Effect of Urea, Carbopol and Xanthan Gum on Hair Removal

The compositions in Table 12 were produced according to the method given above for Example 8 except that no AMP is included in the compositions.

TABLE 12 compositions comprising urea, carbopol and xanthan gum

| Ingredients | Ex 9a (% wt) | Ex 9b (% wt) |
|---|---|---|
| Xanthan gum FN | 0.8 | 0.8 |
| Urea | 8.0 | 8.0 |
| Acrylates Copolymer*[4] | 1.0 | — |
| Lithium Magnesium Sodium Silicate*[8] | — | 1.0 |
| Sodium Gluconate | 0.1 | 0.1 |
| Paraffin oil | 5.0 | 5.0 |
| Potassium Hydroxide 50% soln*[2] | 5.16 | 4.09 |
| Potassium Thioglycolate (TGK) 44.5% solution*[1] | 10.0 | 10.0 |
| Ceteareth 20 | 0.4 | 0.4 |
| Cetearyl alcohol | 3.5 | 3.5 |
| Glycerin | 5.0 | 5.0 |
| D.I. water | to 100.0 | to 100.0 |
| pH at 20° C. | 11.539 | 11.583 |

The compositions of Examples 9a and 9b were tested to determine their efficacy for hair removal by following the method given for Example 8. The results of the hair testing are shown in Table 13 below:

TABLE 13 the efficacy of compositions 9a and 9b on hair removal

| | Hair removal results | |
|---|---|---|
| | Ex 9a | Ex 9b |
| Preferred optional ingredients | Carbopol, urea, xanthan gum | Lithium Magnesium Sodium Silicate, urea, xanthan gum |
| % hair removal | 63.3 | 55.27 |

The above results demonstrate that the combination of the Carbopol, urea and xanthan gum provides a greater degree of hair removal than the combination of the Lithium Magnesium Sodium Silicate, urea and xanthan gum even in the absence of AMP.

What is claimed is:

1. A depilatory composition comprising:
a depilatory active, wherein the depilatory active is present in an amount of from 0.5 to 10 wt % based on the weight of the depilatory composition, and wherein the depilatory active contains a thiol group and is selected from the group consisting f potassium thioglycolate, calcium thioglycolate, thioglycolic acid, dithioerythritol, thioglycerol, thioglycol, thioxanthine, thiosalicylic acid, N-acetyl-L-cysteine, lipoic acid, sodium dihydrolipoate 6,8-dithiooctanoate, sodium 6,8-diothiooctanoate, a hydrogen sulphide salt, 2-mercaptopropionic acid, 3-mercaptopropionic acid, thiomalic acid, ammonium thioglycolate, glyceryl monothioglycolate, monoethanolamine thioglycolate, monoethanolamine thioglycolic acid, diammoniumdithiodiglycolate, ammonium thiolactate, monoethanolamine thiolactate, thioglycolamide, homocysteine, cysteine, glutathione, dithiothreitol, dihydrolipoic acid, 1,3-dithiopropanol, thioglycolamide, thioglycol-hydrazine, keratinase, guanidine thioglycolate, cysteamine, and combinations thereof;
an alkali metal hydroxide selected from the group consisting of sodium hydroxide and/or potassium hydroxide; and
an aminoalkylpropanol, wherein the aminoalkylpropanol is present in an amount of from 0.2 to 10 wt % based on the weight of the depilatory composition; and
wherein at 20° C. the composition has a pH in the range of from 10 to 12.5.

2. The depilatory composition according to claim 1, wherein the composition is in a form selected from the group consisting of a gel, mousse, foam, cream, lotion or peelable film.

3. The depilatory composition according to claim 1, wherein the depilatory composition is one of transparent and translucent.

4. The depilatory composition according to claim 3, wherein the depilatory composition is in the form of a gel.

5. The depilatory composition according to claim 1, wherein the depilatory active comprises one or both of potassium thioglycolate and thioglycolic acid.

6. The depilatory composition according to claim 1, wherein the depilatory active is present in an amount of from 1.5 to 7 wt % based on the weight of the depilatory composition.

7. The depilatory composition according to claim 1, wherein the alkali metal hydroxide is potassium hydroxide.

8. The depilatory composition according to claim 1, wherein the alkali metal hydroxide is present in a total amount of 0.5 to 5 wt % based on the weight of the depilatory composition.

9. The depilatory composition according to claim 7, wherein the composition comprises 0.5 to 5 wt % potassium hydroxide based on the weight of the depilatory composition.

10. The depilatory composition according to claim 1, wherein the aminoalkylpropanol comprises aminomethylpropanol.

11. The depilatory composition according to claim 1, wherein the aminoalkylpropanol is present in an amount of from 0.5 to 10 wt % based on the weight of the depilatory composition.

12. The depilatory composition according to claim 1, wherein the aminoalkylpropanol is present in an amount of from 0.75 to 4.5 wt % based on the weight of the depilatory composition.

13. The depilatory composition according to claim 1, wherein the weight ratio of the aminoalkylpropanol to alkali metal hydroxide is in the range of from 3:1 to 1:1.

14. The depilatory composition according to claim 1, wherein the composition has a pH in the range of 10.2 to 12.

15. The depilatory composition according to claim 5, wherein the composition comprises potassium thioglycolate and/or thioglycolic acid, potassium hydroxide and aminomethylpropanol.

16. The depilatory composition according to claim 1, wherein the composition comprises from 2 to 6 wt % potassium thioglycolate and/or thioglycolic acid, from 0.5 to 5 wt % potassium hydroxide and from 0.75 to 4.5 wt % aminomethylpropanol, each based on the weight of the depilatory composition.

17. The depilatory composition according to claim 1, wherein the composition comprises a carbomer.

18. The depilatory composition according to claim 1, wherein the composition comprises urea.

19. The depilatory composition according to claim 1, wherein the composition comprises a gum.

20. The depilatory composition according to claim 1, wherein the composition comprises xanthan gum.

21. The depilatory composition according to claim 1 further comprising:
a carbomer;
urea; and
xanthan gum.

22. A method of removing hair from the bodily surface of a mammal, the method comprising:
applying the composition according to claim 1 to the bodily surface of a mammal from where it is desired to remove hair;
allowing the composition to contact the bodily surface for a period of time of from 1 to 10 minutes; and
subsequently removing at least a portion of the composition from the bodily surface.

23. The method according to claim 22, wherein the step of allowing the composition to contact the bodily surface is for between 2 to 8 minutes.

24. A method of producing the composition according to claim 1, the method comprising:
providing an intermediate composition comprising the depilatory active and the alkali metal hydroxide; and
adding the aminoalkylpropanol to the intermediate composition.

* * * * *

UNITED STATES PATENT AND TRADEMARK OFFICE
CERTIFICATE OF CORRECTION

| | | |
|---|---|---|
| PATENT NO. | : 12,364,656 B2 | Page 1 of 1 |
| APPLICATION NO. | : 17/685732 | |
| DATED | : July 22, 2025 | |
| INVENTOR(S) | : Lorea Oria Martinez et al. | |

It is certified that error appears in the above-identified patent and that said Letters Patent is hereby corrected as shown below:

In the Specification

Column 12, Line 67: Delete "10000" and replace with -- 100% --.

Signed and Sealed this
Thirtieth Day of September, 2025

John A. Squires
*Director of the United States Patent and Trademark Office*